(12) United States Patent
Zoeller et al.

(10) Patent No.: US 7,582,792 B2
(45) Date of Patent: Sep. 1, 2009

(54) CARBONYLATION PROCESS

(75) Inventors: Joseph Robert Zoeller, Kingsport, TN (US); Mary Kathleen Moore, Jonesborough, TN (US); Andrew James Vetter, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 378 days.

(21) Appl. No.: 11/424,327

(22) Filed: Jun. 15, 2006

(65) Prior Publication Data

US 2007/0293695 A1 Dec. 20, 2007

(51) Int. Cl.
C07C 67/36 (2006.01)
C07C 51/12 (2006.01)

(52) U.S. Cl. .............. 560/204; 562/519; 560/232

(58) Field of Classification Search ............. 560/232, 560/204; 562/519
See application file for complete search history.

(56) References Cited

U.S. PATENT DOCUMENTS

| | | | |
|---|---|---|---|
| 3,689,533 A | 9/1972 | Schultz | |
| 3,717,670 A | 2/1973 | Schultz | |
| 3,772,380 A | 11/1973 | Paulik et al. | |
| 3,927,078 A | 12/1975 | Lapporte et al. | |
| 4,046,807 A | 9/1977 | Kuckertz | |
| 4,115,444 A | 9/1978 | Rizkalla | |
| 4,252,741 A | 2/1981 | Porcelli et al. | |
| 4,333,884 A | 6/1982 | Kubbeler et al. | |
| 4,358,411 A | 11/1982 | Porcelli et al. | |
| 4,366,259 A | 12/1982 | Knifton et al. | |
| 4,374,070 A | 2/1983 | Larkins et al. | |
| 4,417,077 A | 11/1983 | Drago et al. | |
| 4,430,273 A | 2/1984 | Erpenbach et al. | |
| 4,484,002 A * | 11/1984 | Lin ..................... | 560/232 |
| 4,559,183 A | 12/1985 | Hewlett | |
| 4,629,809 A | 12/1986 | Vanderpool et al. | |
| 5,003,104 A | 3/1991 | Paulik et al. | |
| 5,144,068 A | 9/1992 | Smith et al. | |
| 5,258,549 A | 11/1993 | Pimblett | |
| 5,292,948 A | 3/1994 | Zoeller | |
| 5,298,586 A | 3/1994 | Beevor et al. | |
| 5,380,929 A | 1/1995 | Erpenbach et al. | |
| 5,416,237 A | 5/1995 | Aubigne et al. | |
| 5,442,107 A | 8/1995 | Beevor et al. | |
| 5,488,143 A | 1/1996 | Uhm et al. | |
| 5,510,524 A | 4/1996 | Garland et al. | |
| 5,705,683 A | 1/1998 | Lippert et al. | |
| 5,760,284 A | 6/1998 | Zoeller | |
| 5,866,716 A | 2/1999 | Schafer et al. | |
| 5,900,505 A | 5/1999 | Tustin et al. | |
| 5,922,911 A | 7/1999 | Jones et al. | |
| 5,936,117 A | 8/1999 | Zoeller et al. | |
| 5,977,407 A | 11/1999 | Zoeller | |
| 6,130,355 A | 10/2000 | Jones | |
| 6,211,405 B1 | 4/2001 | Cheung et al. | |
| 6,452,043 B1 | 9/2002 | Zoeller et al. | |
| 6,472,565 B1 | 10/2002 | Bahrmann et al. | |
| 6,667,418 B2 | 12/2003 | Broussard et al. | |
| 6,916,951 B2 | 7/2005 | Tustin et al. | |
| 7,115,774 B2 | 10/2006 | Magna et al. | |
| 2005/0049434 A1 | 3/2005 | Tustin et al. | |

FOREIGN PATENT DOCUMENTS

| | | |
|---|---|---|
| EP | 0008396 A1 | 5/1980 |
| EP | 0109212 A | 5/1984 |
| EP | 0087870 B1 | 4/1985 |
| EP | 0096974 B1 | 9/1985 |
| EP | 0153834 | 9/1985 |
| EP | 0087869 B1 | 7/1986 |
| EP | 0338730 A1 | 10/1989 |
| EP | 0391680 | 10/1990 |
| EP | 0584964 | 3/1994 |
| EP | 0752406 | 1/1997 |
| EP | 0976711 | 2/2000 |
| EP | 0081152 A | 6/2006 |
| GB | 2029409 | 3/1890 |
| JP | 146933 | 5/2003 |
| WO | 99/54273 | 10/1999 |

OTHER PUBLICATIONS

Howard et al, Catalysis Today, 18, (1993) pp. 325-354.
Fujimoto et al, Chemistry Letters (1987) pp. 895-898.
Fujimoto et al, Journal of Catalysis, 133 (1992) pp. 370-382.
Welton, Chemical Reviews, 99, (1999) pp. 2071-2083.
Knifton, J. Catal., 96, (1985) pp. 439-453.
Mizushima et al, Green Chemistry, 3, (2001) pp. 76-79.
Chauvin et al, Chem. Int. Engl., 34, (1995) pp. 2698-2700.
Yagita et al, Catalysis Letters, 2, (1989) pp. 145-148.
Riisager et al, "First Application of supported ionic liquid phase (SILP) catalysis for continuous methanol carbonylation", Chem. Commun., 2006, pp. 994-996.
W. Bertleff, Carbonylation, Ulmann's Encyclopedia of Industrial Chemistry, 6th Edition, vol. 6, Wiley-VCH Verlag GmbH & Co. KGaA, Weinheim, Germany, (2003) p. 473.

(Continued)

*Primary Examiner*—Taylor Victor Oh
(74) *Attorney, Agent, or Firm*—Eric D. Middlemas; Bernard J. Graves, Jr.

(57) ABSTRACT

Disclosed is a carbonylation process for the production of carboxylic acids, carboxylic acid esters and/or carboxylic acid anhydrides wherein a carbonylation feedstock compound selected from one or more organic oxygenates such as alcohols, ethers, and esters is contacted with carbon monoxide in the presence of a carbonylation catalyst and one or more onium compounds. The carbonylation process differs from known carbonylation processes in that a halide compound such as a hydrogen halide, typically hydrogen iodide, and/or alkyl halide, typically methyl iodide, extraneous or exogenous to the carbonylation process is not fed or supplied separately to the process.

18 Claims, No Drawings

OTHER PUBLICATIONS

W. Rienmenschneider, "Carboxylic Acids, Aliphatic", Ulmann's Encyclopedia of Industrial Chemistry, 6th Edition, vol. 6, Wiley-VCH Verlag GmbH & Co. KGaA, Weinheim, Germany, (2003) p. 493.

Yoneda et al, "Recent advances in processes and catalysts for the production of acetic acid", Applied Catalysis A: General 221 (2001) 253-265.

De Blasio, "Activity and Stability of Two Polymer-Supported Rhodium-Based Catalysts for the Vapour Phase Carbonylation of Methanol", Journal of Catalysis, 176, (1998) 253-359.

Sunley et al, "High productivity methanol carbonylation catalysis using iridium The Cativa(TM) process for the manufacture of acetic acid", Catalysis Today, 58, (2000) 293-307.

Zhao et al, "Ionic liquids: applications in catalysis", Catalysis Today, 74, (2002) 157-189.

Riisager et al, "Very Stable and Highly Regioselective Supported Ionic-Liquid-Phase (SILP) Catalysis:Continuous-Flow Fixed-Bed Hydroformylation of Propene", Angew. Chem. Int. Ed. 2005, 44, 815-819.

Mehnert, "Supported Ionic Liquid Catalysis", Chem. Eur. J. 2005, 11, 50-56.

Riisager et al, "Supported Ionic Liquid Phase (SILP) Catalysis: An Innovative Concept for Homogenous Catalysis in Continuous Fixed-Bed Reactors", Eur. J. Inorg. Chem. (2006), 695-706.

Drago et al, "Ionic Attachment as a Feasible Approach to Heterogenizing Anionic Solution Catalysts, Carbonylation of Methanol", Inorganic Chemistry, vol. 20, No. 3, (1981) 641-644.

Haynes et al, "Structure and reactivity of polymer-supported carbonylation catalysts", J. Chem. Soc., Dalton Trans., (2002) 2565-2572.

Welton, "Ionic Liquids in Catalysis", Coordination Chemistry Reviews 248 (2004) 2459-2477.

Riisager et al, "Stability and Kinetic Studies of Supported Ionic Liquid Phase Catalysts for Hydroformylation of Propene", Ind. Eng. Chem. Res., (2005) 44, 9853-9859.

Wasserscheid, Peter and Keim, Wilhem, "Ionic Liquids—New Solutions for Transition Metal Catalysis", Angew. Chem. Int. Ed., 2000, 39, 3772-3789.

Copending U.S. Appl. No. 11/426,326, filed Jun. 26, 2006, Zoeller et al.

Danish application titled "A process for continuous carbonylation by supported ionic liquid-phase catalysis" (Unpublished patent application provided by inventor and believed to be related to Denmark Patent Application No. 2005/00735, filed May 20, 2005, and PCT application Serial No. PCT/DK2006/000275).

Zoeller et al., "Rhodium Catalyzed Carbonylation of Ethylene and Methanol in the Absence of Alkyl Halides Using Ionic Liquids," Organic Reactions Catalysis Society, pp. 1-11 (to be published).

Article, "Recent advances in processes and catalysts for the production of acetic acid," Applied Catalysis A: General 221 (2001) pp. 253-265.

Rangits et al., "Palladium catalysed hydroethoxycarbonylation in imidazolium-based ionic liquids," Journal of Molecular Catalysis A: Chemical 246 (2006) 59-64.

Samel et al. "Proprionic Acid and Derivatives," Ulmann's Encyclopedia of Industrial Chemistry, 6th Edition, vol. 30, Wiley-VCH Verlag GmbH & Co. KGaA, Weinheim, Germany (2003) p. 261.

Copending U.S. Appl. No. 12/060,741, filed Apr. 1, 2008, Zoeller et al.

Office Action dated Aug. 22, 2008 in copending U.S. Appl. No. 12/060,741, filed Apr. 1, 2008, Zoeller et al.

Office Action dated Mar. 6, 2009 in copending U.S. Appl. No. 12/060,741, filed Apr. 1, 2008, Zoeller et al.

Office action dated Jun. 26, 2007, in copending U.S. Appl. No. 11/426,326, filed Jun. 26, 2006, Zoeller et al.

Office action dated Aug. 31, 2007, in copending U.S. Appl. No. 11/426,326, filed Jun. 26, 2006, Zoeller et al.

Office action dated Feb. 28, 2008, in copending U.S. Appl. No. 11/426,326, filed Jun. 26, 2006, Zoeller et al.

Office action dated Apr. 11, 2008, in copending U.S. Appl. No. 11/426,326, filed Jun. 26, 2006, Zoeller et al.

Notice of Allowance dated Oct. 22, 2008, in copending U.S. Appl. No. 11/426,326, filed Jun. 26, 2006, Zoeller et al.

Notice of Allowance dated Mar. 24, 2009, in copending U.S. Appl. No. 11/426,326, filed Jun. 26, 2006, Zoeller et al.

* cited by examiner

CARBONYLATION PROCESS

FIELD OF THE INVENTION

This invention pertains to a carbonylation process for the production of carboxylic acids, carboxylic acid esters and/or carboxylic acid anhydrides wherein a carbonylation feedstock compound selected from one or more organic oxygenates such as alcohols, ethers, and esters is contacted with carbon monoxide in the presence of a carbonylation catalyst and one or more onium compounds. More specifically, this invention pertains to a carbonylation process wherein, unlike known carbonylation processes, a halide compound such as a hydrogen halide, typically hydrogen iodide, and/or alkyl halide, typically methyl iodide, exogenous or extraneous to the carbonylation process is not fed or supplied separately to the process. The present carbonylation process thus avoids the handling and storage of hazardous and corrosive hydrogen and alkyl halides.

BACKGROUND OF THE INVENTION

Processes for the manufacture of acetic acid from methanol by carbonylation are operated extensively throughout the world. A thorough review of these commercial processes and other methods for the production of acetyl compounds from single carbon sources are described by Howard et al. in *Catalysis Today*, 18 (1993) 325-354. All commercial carbonylation processes for the preparation of acetic acid involve feeding methanol, a halogen compound, typically hydrogen iodide and/or methyl iodide, and a solvent such as acetic acid to a reaction zone wherein the feed materials are contacted with carbon monoxide and a Group VIII catalyst, typically a rhodium catalyst. The liquid reaction mixture is removed from the reaction zone and the product acetic acid and/or other acetyl compound is recovered from the liquid. In the most important carbonylation processes, i.e., the conversion of methanol to acetic acid and the conversion of methyl acetate to acetic anhydride, hydrogen iodide and/or methyl iodide normally are fed to the reaction zone wherein the carbonylation reaction occurs. The feed of hydrogen iodide and/or methyl iodide is problematic since the hydrogen iodide and/or methyl iodide are corrosive, must be removed from the product and recycled in subsequent distillation steps, and due to its toxicity and volatility, requires very rigorous and expensive process controls. Elimination of the requirement to add this large volume of methyl iodide would reduce significantly the costs associated with separation and the expensive control equipment associated with safely handling such a volatile and toxic component.

A review of these processes is available in Howard, et. al., *Catalysis Today*, 18, 325-354 (1993). Included in the Howard et. al. article is a listing of attempts to develop an alkyl halide-free carbonylation system (see pages 345-347). However, all previous attempts have failed to provide a commercially-viable process since alkyl halide-free carbonylation processes give very slow reaction rates, proceeding at about 1% or less of the rates of the commercial process.

BRIEF SUMMARY OF THE INVENTION

We have developed a carbonylation process which neither utilizes nor requires the introduction or feed of an iodide compound, i.e., hydrogen iodide or an alkyl iodide, in the production of carboxylic acids or esters or anhydrides thereof. The present invention provides a carbonylation process for the production of a carbonylation product selected from carboxylic acids, carboxylic acid esters, carboxylic acid anhydrides or a mixture of any two or more thereof which comprises combining in a reaction zone (i) a carbonylation feedstock compound selected from alkanols, dialkyl ethers, carboxylic acid esters or a mixture of any two or more thereof, (ii) a Group VIII metal carbonylation catalyst, (iii) an onium salt compound and (iv) carbon monoxide under carbonylation conditions of pressure and temperature, wherein neither hydrogen halide nor an alkyl halide exogenous or extraneous to the carbonylation process is added or supplied to the reaction zone.

DETAILED DESCRIPTION

The carbonylation feedstock compound which may be used in the process of the present invention is selected from alkanols, dialkyl ethers and alkyl esters of carboxylic acids. The alkanols include substituted alkanols and may contain from 1 to about 10 carbon atoms. Primary alkanols are preferred with methanol being especially preferred. The dialkyl ethers and alkyl carboxylate esters may contain a total of 2 to about 20 carbons. Dimethyl ether and methyl acetate are the most preferred ethers and esters. Depending on the mode of operation of the process of the present invention, the carbonylation feedstock compound may constitute about 5 to 95 weight percent of the reaction medium or solution, i.e., the total weight of the contents of the reaction zone wherein a carbonylation feedstock compound is contacted with carbon monoxide in the presence of a Group VIII metal carbonylation catalyst and an onium salt compound.

Although the presence of water in the carbonylation feedstock compound is not essential when the feedstock compound is an alkanol, the presence of some water is desirable to suppress formation of carboxylic acid esters and/or dialkyl ethers. When using an alkanol to produce a carboxylic acid, the molar ratio of water to alkanol may be about 0:1 to 10:1, but preferably is in the range of about 0.01:1 to 1:1. When the carbonylation feedstock compound is a carboxylic acid ester or dialkyl ether, the amount of water fed typically is increased to account for the mole of water required for hydrolysis of the alkanol alternative. Therefore, when using either a carboxylic acid ester or dialkyl ether, the mole ratio of water to ester or ether is in the range of about 1:1 to 10:1, but preferably in the range of about 1:1 to 3:1. In the preparation of a carboxylic acid, it is apparent that combinations of alkanol, alkyl carboxylic acid ester, and/or dialkyl ether are equivalent, provided the appropriate amount of water is added to hydrolyze the ether or ester to provide the methanol reactant. When the process is operated to produce a carboxylic acid ester, preferably no water should be added and a dialkyl ether becomes the preferred feedstock. Further, when an alkanol is used as the feedstock in the preparation of a carboxylic acid ester, it is preferable to remove water.

Products that may be obtained from the present process include carboxylic acids of 2-13 carbons, carboxylic acid anhydrides containing 4 to about 21 carbons, and alkyl carboxylate esters containing 3 to about 21 carbons. The most useful application of the process of the present invention is in production of $C_2$ to $C_4$ carboxylic acids such as acetic acid from methanol and propionic acid from ethanol. For example, the carbonylation product can be acetic acid, methyl acetate, acetic anhydride, or a mixture of any two or more thereof.

The Group VIII metal carbonylation catalyst may be selected from a variety of compounds of the metals in Groups 8, 9, and 10, i.e., Fe, Ru, Os, Co, Rh, Ir, Ni, Pd and Pt of the periodic table traditionally referred to as the Group VIII metals, in prior terminology. Co, Rh, Ir, Ni, and Pd and compounds and complexes thereof are preferred with compounds and complexes of Rh and Ir being especially preferred. Any form of these metals may be used and they may be used as single components or in combination with one another. The Group VIII metal carbonylation catalysts may be employed in combination with promoters or co-catalysts such as alkali metal compounds, group 6 metal (Cr, Mo, W) compounds, alkaline earth metal compounds and compounds of zinc, tin and Lanthanide metals. Additional ligands such as tertiary amines and phosphines, i.e., unquarternized or non-protonated amines and phosphines, also may be present although they are not necessarily required for efficient operation of the process. The Group VIII metal carbonylation catalysts typically are used in concentrations between about 0.0001 mol to 1 mol per kg of reaction medium or solution. The more active of the Group VIII metal carbonylation catalysts typically are used in concentrations of about 0.001 to 0.1 mol per kg of reaction medium or solution.

The carbonylation process of the present invention is carried out in the presence of an onium salt comprising a cation selected from quaternary atoms or radicals such as quaternary ammonium, quaternary phosphonium, trialkyl sulfonium, and alkylated sulfoxide. The onium salt compound may be functional and includes protonated forms of the atoms or radicals, especially protonated forms of various tertiary amines and tertiary phosphines. The onium salt may contain any number of carbon atoms, e.g., up to about 60 carbon atoms, and also may contain one or more heteroatoms. The tri- and tetra-alkyl quaternary ammonium and phosphonium salts typically contain a total of about 5 to 40 carbon atoms.

Examples of quaternary ammonium and phosphonium salts include salts of cations having the formula

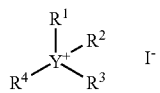

wherein $R^1$, $R^2$, $R^3$, and $R^4$ are independently selected from alkyl or substituted alkyl moieties having up to about 20 carbon atoms, cycloalkyl or substituted cycloalkyl having about 5 to about 20 carbon atoms, or aryl or substituted aryl having about 6 to about 20 carbon atoms; and Y is N or P. The quaternary ammonium salts also may be selected from salts of aromatic, heterocyclic onium cations having the formula

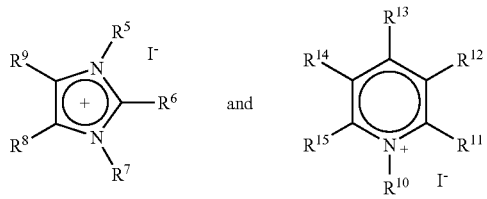

wherein at least one ring atom is a quaternary nitrogen atom and $R^6$, $R^8$, $R^9$, $R^{11}$, $R^{12}$, $R^{13}$, $R^{14}$, and $R^{15}$ are independently selected from hydrogen, alkyl or substituted alkyl moieties having up to about 20 carbon atoms, cycloalkyl or substituted cycloalkyl having about 5 to about 20 carbon atoms, or aryl or substituted aryl having about 6 to about 20 carbon atoms; and $R^5$, $R^7$, and $R^{10}$ are independently selected from alkyl or substituted alkyl moieties having up to about 20 carbon atoms, cycloalkyl or substituted cycloalkyl having about 5 to about 20 carbon atoms, or aryl or substituted aryl having about 6 to about 20 carbon atoms.

Examples of specific ammonium salts include tetrapentylammonium iodide, tetrahexylammonium iodide, tetraoctylammonium iodide, tetradecylammonium iodide, tetradodecylammonium iodide, tetrapropylammonium iodide, tetrabutylammonium iodide, methyltrioctylammonium iodide, methyltributylammonium iodide, N-octyl-quinuclidinium iodide, N,N'-dimethyl-N,N'-dihexadecylpiperazinium diiodide, dimethyl-hexadecyl-[3-pyrrolidinylpropyl]ammonium iodide, N,N,N,N',N',N'-hexa(dodecyl)-octane-1,8-di-ammonium diiodide, N,N,N,N',N',N'-hexa(dodecyl)butane-1,4-di-ammonium diiodide; imidazolium iodides such as 1-butyl-3-methylimidazolium iodide, 1,3-dimethylimidazolium iodide, 1,3,4-trimethylimidazolium iodide, 1,2,3,4,5-pentamethylimidazolium iodide; pyridinium iodides such as N-octylpyridinium iodide, N-methylpyridinium iodide, N-methyl-2-picolinium iodide, N-methyl-3-picolinium iodide, N-methyl-4-picolinium iodide, N-methyl-5-ethyl-2-methyl-pyridinium iodide, N-methyl-3,4-lutidinium iodide; N-methyl quinolinium iodide, N-methyl isoquinolinium iodide or mixtures thereof. Preferred quaternary ammonium iodides include 1-butyl-3-methylimidizolium iodide, N-methyl pyridinium iodide, N-methyl-5-ethyl-2-methyl-pyridinium iodide, and 1,3-dimethylimidazolium iodide. Exemplary phosphonium compounds include tetraoctylphosphonium iodide, tetrabutylphosphonium iodide, triphenyl(hexyl)phosphonium iodide, triphenyl(octyl)phosphonium iodide, tribenzyl(octyl)phosphonium iodide, tribenzyl(dodecyl)phosphonium iodide, triphenyl(decyl)phosphonium iodide, triphenyl(dodecyl)phosphonium iodide, tetrakis(2-methylpropyl)phosphonium iodide, tris(2-methylpropyl)(butyl)phosphonium iodide, triphenyl(3,3-dimethylbutyl)phosphonium iodide, triphenyl(3-methylbutyl)phosphonium iodide, tris(2-methylbutyl)(3-methylbutyl)phosphonium iodide, triphenyl[2-trimethylsilylethyl]phosphonium iodide, tris(p-chlorophenyl)(dodecyl)phosphonium iodide, hexyltris(2,4,6-trimethylphenyl)phosphonium iodide, tetradecyltris(2,4,6-tri-methylphenyl)phosphonium iodide, dodecyltris(2,4,6-trimethylphenyl)phosphonium iodide, methyltriocytlphosphonium iodide, methyltributylphosphonium iodide, methyltricyclohexylphosphonium iodide, and the like. Preferred phosphonium iodides include methyltriphenylphosphonium iodide, methyltributylphosphonium iodide, methyltriocytlphosphonium iodide, and butyltridodecylphosphonium iodide.

The onium salt also may be a polymer containing quaternary nitrogen groups such as polymers and copolymers derived in whole or part from (or containing polymerized residues of) 2- or 4-vinyl-N-alkylpyridinium halides or 4-(trialkylammonium)styrene halides. The most preferred onium salts comprise N-alkyl-pyridinium halides and N,N'-(or 1,3-) dialkylimidazolium halides wherein the alkyl groups contain 1 to about 4 carbon atoms. The iodide salts are especially preferred. The onium salts may consist of one or more quaternary cations and/or one or more anions. The anion(s) of the onium salts may be selected from a wide variety of species such as halides, carboxylates, tetraflouroborate, hexahalophosphates, bis (trifluoro-methanesulfonyl)amide [$(CF_3SO_2)_2N^-$], and anionic metal complexes such as $(CO)_4Co^-$, trihalozincates, ($ZnX_3^-$, X=F,Cl,Br, I), trichlorostannates ($SnCl_3^-$) diododicarbonylrhodate (I) and diiododicarbonyliridate (I) and may be mixtures of anions. However, the most useful anions are the halides and carboxylates or mixtures thereof both from ease of manufacture and function in the carbonylation process. The iodide salts are especially preferred. The onium salt typically constitutes about 5 to 95 weight percent of the reaction medium or solution depending on the particular onium salt employed and the mode of operation of the carbonylation process.

The onium salts may be prepared according to various procedures known in the art. The most efficient method for preparing the preferred halide salts is to simply alkylate or protonate the amine or phosphine precursor with an alkyl or hydrogen halide. Due to their ease of preparation and availability of the amine and phosphine precursors, the most preferred onium salts for a liquid phase operation are selected from the group of salts consisting of quaternary ammonium and phosphonium halides, with the most preferred being halide salts derived from pyridine and imidazole derivatives. The following example illustrates one technique for the preparation of the preferred onium salt—1,3-dimethylimidazolium iodide: To a single neck, 2-liter flask equipped with magnetic-stir bar, nitrogen inlet, condenser and an addition flask, was added 140 grams of 1 -methylimidazole (1.705 moles) and 600 ml of ethyl acetate. Iodomethane (266 grams, 1.876 moles) was added drop-wise over a period of 1 hour to control the exotherm. The reaction mixture was stirred overnight at room temperature. The liquid was decanted and the solids were washed with ethyl acetate and dried on a rotary evaporator for 1 hour at 60° C. under 0.1 mbar of pressure. The 1,3-dimethylimidazolium iodide product (381 g, 1.701 moles, 99.7% mass yield) was a crystalline solid and was spectroscopically pure by NMR. Similar results are obtained using tetrahydrofuran (THF) as solvent.

The carbon monoxide may be fed to the reaction or carbonylation zone either as purified carbon monoxide or as carbon monoxide including other gases. The carbon monoxide need not be of high purity and may contain from about 1% by volume to about 100% by volume carbon monoxide, and preferably from about 70% by volume to about 99% by volume carbon monoxide. The remainder of the gas mixture may include such gases as nitrogen, hydrogen, water and parafinic hydrocarbons having from one to four carbon atoms. Although hydrogen is not part of the reaction stoichiometry, hydrogen may be useful in maintaining optimal catalyst activity. Therefore, the preferred ratio of carbon monoxide to hydrogen is in the range of about 99:1 to about 2:1, but ranges with even higher hydrogen levels are also useful. The amount of carbon monoxide useful for the carbonylation reaction ranges from a molar ratio of about 0.1:1 to about 1,000:1 of carbon monoxide to alcohol, ether or ester equivalents with a more preferred range being from about 0.5:1 to about 100:1 and a most preferred range from about 1.0:1 to about 20:1.

The carbonylation conditions of pressure and temperature may vary significantly depending upon various factors such as, for example, the mode of operation, the Group VIII catalyst employed, the process apparatus utilized and the degree of conversion of the carbonylation feedstock that is desired. For example the process may be operated under a pressure (total) ranging from atmospheric pressure to 250 bar gauge (barg; 3700 pounds per square inch gauge—psig). However, pressures (total) in the range of about 5 to 100 barg (72.5 to 1450 psig) are more typical with pressures in the range of about 10 to 80 barg being preferred when using the preferred rhodium as the Group VIII metal carbonylation catalyst. The process temperature may range from about 50 to 300° C. although temperatures in the range of about 150 to 250° C. are more typical.

In the carbonylation process provided by the present invention neither hydrogen halide nor an alkyl halide exogenous or extraneous to the carbonylation process is added or supplied to the reaction zone, i.e., fresh hydrogen halide and/or fresh alkyl halide are not fed to the reaction zone of the process. Minor amounts, i.e., minor as compared to known processes, of such halides, e.g., methyl iodide, may form during operation of the process by reaction of a feedstock compound, or fragment of a feedstock compound, with a halide anion of the onium salt compound. In continuous operation of the carbonylation process, a low boiling stream is recovered from the product recovery and refining section of the process. This low boiling stream normally is recycled to the reaction zone of the carbonylation process.

The carbonylation process provided by the present invention provides a means for preparing a carbonylation product selected from carboxylic acids, carboxylic acid esters, carboxylic acid anhydrides or a mixture of any two or more thereof. The process may be carried out using any of a variety of operational modes. The following process modes of operation are representative:

(1) A process comprising the steps of:
    (i) feeding to a reaction zone (i) a carbonylation feedstock compound selected from alkanols, dialkyl ethers, carboxylic acid esters or a mixture of any two or more thereof, (ii) a Group VIII metal carbonylation catalyst, (iii) an onium salt compound and, optionally, an inert solvent to provide a homogeneous reaction zone liquid and feeding carbon monoxide to the homogeneous reaction zone liquid under carbonylation conditions of pressure and temperature; and
    (ii) removing from the reaction zone a crude liquid product comprising carbonylation product, carbonylation feedstock compound, Group VIII metal carbonylation catalyst, onium salt compound, optional inert solvent and carbon monoxide;

wherein neither hydrogen halide nor an alkyl halide exogenous or extraneous to the carbonylation process is added to the reaction zone.

(2) A process comprising the steps of:
    (i) feeding a carbonylation feedstock compound selected from alkanols, dialkyl ethers, carboxylic acid esters or a mixture of any two or more thereof and carbon monoxide to a reaction zone containing a solution comprising a Group VIII metal carbonylation catalyst and an onium salt compound to provide a homogeneous reaction zone liquid maintained under carbonylation conditions of pressure and temperature wherein the temperature of the reaction zone is maintained above the dew point of the carbonylation product; and
    (ii) removing from the reaction zone a crude gaseous product comprising carbonylation product, carbonylation feedstock compound and carbon monoxide;

wherein neither hydrogen halide nor an alkyl halide exogenous or extraneous to the carbonylation process is added to the reaction zone.

(3) A process comprising the steps of:
    (i) feeding gaseous carbonylation feedstock compound selected from alkanols, dialkyl ethers, carboxylic acid esters or a mixture of any two or more thereof and carbon monoxide to a reaction zone containing a heterogeneous or solid Group VIII metal carbonylation catalyst and a heterogeneous or solid onium salt compound (1) deposited on a catalyst support material or (2) in the form of a polymeric material containing quaternary nitrogen groups wherein the reaction zone is maintained under carbonylation conditions of pressure and temperature wherein the temperature of the reaction zone is maintained above the dew point of the carbonylation product; and (ii) removing from the reaction zone a crude gaseous product comprising carbonylation product, carbonylation feedstock compound and carbon monoxide;

wherein neither hydrogen halide nor an alkyl halide exogenous or extraneous to the carbonylation process is added to the reaction zone.

Mode (1) is carried out using a homogeneous liquid reaction medium or reaction zone maintained at a temperature of about 100 to 250° C. and a pressure (total) of about 5 to 80 barg. The homogeneous liquid reaction medium typically comprises about 10 to 80 weight percent of carbonylation feedstock compound, about 10 to 80 weight percent carbonylation product, about 10 to 80 weight percent onium salt and about 0 to 50 weight percent of an optional inert solvent. The optional inert solvent preferably is a carboxylic acid, preferably the carboxylic acid corresponding to the carbonylation product, e.g., acetic acid when the carbonylation product is acetic acid or acetic anhydride. Carbonylation product is recovered from the crude liquid product removed from the reaction zone. The remainder of the crude product comprises a low boiling fraction comprising unreacted carbonylation feedstock compound and a high boiling fraction comprising Group VIII metal carbonylation catalyst, onium salt compound and optional inert solvent. Normally some or all of the low boiling and high boiling fractions are recovered from the crude liquid product and recycled directly or indirectly to the reaction zone. Thus, continuous operation of mode (1) of the process includes the steps of:

(iii) refining the crude liquid carbonylation product to recover (1) carbonylation product, (2) a low boiling fraction comprising carbonylation feedstock compound and (3) a high boiling fraction comprising Group VIII metal carbonylation catalyst, onium salt compound and optional inert solvent; and (iv) recycling the low boiling and high boiling fractions to the reaction zone.

Mode (2) is carried out using a homogeneous liquid reaction medium or reaction zone maintained at a temperature above the dew point of the carbonylation product. The carbonylation product, therefore, can be removed from the reaction zone in the gas phase. Since the dew point is a complex function of dilution (particularly with respect to non-condensable gases such as unreacted carbon monoxide, hydrogen, or inert diluent gas), product composition, and pressure, the process may still be operated over a wide range of temperatures, provided the temperature exceeds the dew point of the product effluent. The term "dew point", as used herein, means the temperature, at a given pressure, at which a gas is saturated with respect to its condensable components and at which condensation occurs. The dew point of the carbonylation products of the present invention may be calculated by methods well known to those skilled in the art, for example, as described in Perry's Chemical Engineer's Handbook, $6^{th}$ ed, (McGraw-Hill), pp. 13-25. Dew points for single product or complex mixtures may be calculated using commercially available engineering computer programs, such as Aspen®, also well-known to those skilled in the art. In practice, the process typically operates at a temperature range of 100 to 250° C. Other examples of temperature ranges in which our process may operate include 120 to 240° C. and 150 to 240° C. The pressure (total) of the reaction zone typically is maintained in the range of about 1 to 50 barg. The homogeneous liquid reaction medium may comprise a solution of the Group VIII metal compound in a melt of the onium salt compound or it may comprise a solution of the Group VIII metal compound and the onium salt compound in a high-boiling, i.e., substantially non-volatile under reaction conditions, solvent. Examples of such high-boiling solvents include sulfoxides and sulfones, e.g., dimethyl sulfoxide and sulfolane; amides, e.g., N-methyl-2-pyrrolidinone (NMP), dimethylacetamide, $C_6$ to $C_{30}$ carboxylic acids; aromatic hydrocarbons, e.g., 2-methylnaphthalene; and high-boiling, saturated hydrocarbons, e.g., decalin, dodecane. While the Mode (2) reaction nominally is a vapor phase process and contains little or no detectable carbonylation feedstock or product, the liquid reaction medium or reaction zone typically contains at least a portion of the carbonylation feedstock and product as a solution. Typically, the reaction medium or zone comprises about 1 to 40 weight percent of carbonylation feedstock compound, about 1 to 60 weight percent carbonylation product, about 10 to 100 weight percent onium salt and 0 to about 50 weight percent high-boiling solvent. The carbonylation feedstock compound may be fed to the Mode (2) process either as a vapor or liquid. A liquid feed is converted to a vapor within the reaction zone or preferably in a preheated section of the process apparatus. The effluent from the Mode (2) process is a vapor typically comprised of carbonylation product, unconverted carbonylation feedstock compound and carbon monoxide. Operation of the carbonylation process of the present invention according to Mode (2) is further described in U.S. Pat. No. 6,916,951-B1. Any onium salt, catalyst, optional inert solvent, carbonylation feedstock, or low boiling components or intermediates present in the gaseous product removed from the reaction zone may be separated during product recovery/purification and returned to the reaction zone. Continuous operation of Mode (2) of the process typically includes the steps of:

(iii) refining the crude gaseous carbonylation product to recover (1) carbonylation product and (2) a low boiling fraction comprising carbonylation feedstock compound; and (iv) recycling the low boiling fraction to the reaction zone.

Operation of the process according to Mode (3) is somewhat similar to the Mode (2) operation except that both the Group VIII metal carbonylation catalyst and the onium compound are in heterogeneous forms. The Group VIII metal carbonylation catalyst may be deposited on a catalyst support material such as carbon or an inorganic oxide such as alumina or silica according to known procedures. Alternatively, the onium salt may be generated from polymers containing a quaternary, or quaternizable, phosphine or amine. For example, a variety of 4-vinyl pyridine polymers and copolymers are available, and may be quaternized or protonated with alky halides or hydrogen halides to generate heterogeneous onium salts. Further, polymers of N-methyl-4-vinylpyridium chloride are commercially available and may be used as is or preferably exchanged with iodide by well known means to form the iodide salt. The heterogeneous onium compound may comprise (1) an onium salt compound deposited on a catalyst support material or (2) of a polymeric material containing quaternary nitrogen groups. Examples of such polymeric onium compounds include polymers and co-polymers of vinyl monomers which contain quaternary nitrogen (ammonium) groups. Polymers and copolymers derived from 2- and 4-vinyl-N-alkylpyridinium halides, e.g., poly(4-vinyl-N-methylpyridinium iodide), are specific examples of such polymeric onium salt compounds. In the Mode (3) operation the reaction zone is maintained at a temperature above the dew point of the carbonylation product. Thus, the carbonylation conditions of pressure and temperature employed in Mode (3) are similar to those used in Mode (2). Vapor phase operation wherein an alkyl halide is used is described in U.S. Pat. No. 6,452,043-B1 and US-2005/0049434-A1. Any onium salt, catalyst, optional inert solvent, carbonylation feedstock, or low boiling components or intermediates entrained in the vapor effluent product normally are separated during purification and returned to the reaction zone. Continuous operation of the Mode (3) process typically includes the steps of:

(iii) refining the crude gaseous carbonylation product to recover (1) carbonylation product and (2) a low boiling fraction comprising carbonylation feedstock compound; and (iv) recycling the low boiling fraction to the reaction zone.

EXAMPLES

The processes of the present invention are further illustrated by the following examples wherein the percentages are by weight except for the 5% hydrogen in carbon monoxide wherein the percentage is by volume. The experiments described in the following examples were carried out in an autoclave constructed of Hastelloy® C-276 alloy.

Example 1

To a 300 mL autoclave was added 0.396 g (1.5 millimole—mmol) of $RhCl_3 \cdot 3H_2O$, 112.0 g (0.507 mol) of N-methylpyridinium iodide, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching 190° C. the gas feed was switched to 100% CO and the pressure adjusted to 51.7 barg (750 psig) using 100% CO. The temperature and pressure were maintained for 5 hours using 100% CO as needed to maintain pressure. After 5 hours, the reaction was cooled, vented, and the product transferred to a sample bottle. GC analysis of the product showed that the mixture contained 0.25% methyl acetate, 0.04% methanol, and 55.84% acetic acid. This represents 2.33 moles of acetic acid representing a net production of acetic acid=1.83 moles after accounting for acetic acid in the original solution and 0.008 mol of methyl acetate along with 0.035 moles of unreacted methanol. No methyl iodide was detected in the product by GC analysis.

Example 2

To a 300 mL autoclave was added 0.396 g (1.5 mmol) of $RhCl_3 \cdot 3H_2O$, 112.0 g (0.507 mol) of N-methylpyridinium iodide, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching 190° C. the pressure was adjusted to 51.7 barg (750 psig) using 5% hydrogen in carbon monoxide. The temperature and pressure were maintained for 5 hours using 5% hydrogen in carbon monoxide as needed to maintain pressure. After 5 hours, the reaction was cooled, vented, and the product transferred to a sample bottle. GC analysis of the product showed that the mixture contained 0.09% methyl acetate, and 57.42% acetic acid. This represents 2.52 moles of acetic acid representing a net production of acetic acid=2.02 moles after accounting for acetic acid in the original solution and 0.003 mol of methyl acetate. Neither methyl iodide nor methanol was detected in the product by GC analysis. This example shows that the conversion and selectivity may be enhanced by the presence of hydrogen.

Example 3

To a 300 mL autoclave was added 0.396 g (1.5 mmol) of $RhCl_3 \cdot 3H_2O$, 112.0 g (0.507 mol) of N-methylpyridinium iodide, 3.0 g of water, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching 190° C. the gas feed was switched to 100% CO and the pressure adjusted to 51.7 barg (750 psig) using 100% CO. The temperature and pressure were maintained for 5 hours using 100% CO as needed to maintain pressure. After 5 hours, the reaction was cooled, vented, and the product transferred to a sample bottle. GC analysis of the product shows that the mixture contained 2.83% methyl acetate, 0.04% methanol, and 57.42% acetic acid. This represents 2.5 moles of acetic acid, or a net production of acetic acid=2.0 moles after accounting for acetic acid in the original reaction zone solution, and 0.103 mol of methyl acetate along with 0.003 moles of unreacted methanol. Only a small amount of methyl iodide (0.15% or 0.003 mol) was detected in the product by GC analysis.

Example 4

To a 300 mL autoclave was added 0.396 g (1.5 mmol) of $RhCl_3 \cdot 3H_2O$, 89.6 g (0.40 mol) of N,N'-dimethylimidazolium iodide, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching 190° C. the gas feed was switched to 100% CO and the pressure adjusted to 51.7 barg (750 psig) using 100% CO. The temperature and pressure were maintained for 5 hours using 100% CO as needed to maintain pressure. After 5 hours, the reaction was cooled, vented, and the product transferred to a sample bottle. GC analysis of the product showed that the mixture contained 0.10% methyl acetate, 0.36% methanol, and 59.16% acetic acid. This represents 2.32 moles of acetic acid, a net production of acetic acid=1.82 moles after accounting for acetic acid in the starting reaction zone solution, and 0.003 mol of methyl acetate along with 0.027 moles of unreacted methanol. Only a trace (0.05%, 0.8 mmol) of methyl iodide was detected in the product by GC analysis.

Example 5

To a 300 mL autoclave was added 0.396 g (1.5 mmol) of $RhCl_3 \cdot 3H_2O$, 89.6 g (0.40 mol) of N,N'-dimethylimidazolium iodide, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching 190° C. the pressure was adjusted to 51.7 barg (750 psig) using 5% hydrogen in carbon monoxide. The temperature and pressure were maintained for 5 hours using 5% hydrogen in carbon monoxide as needed to maintain pressure. After 5 hours, the reaction was cooled, vented, and the product transferred to a sample bottle. GC analysis of the product indicated that the mixture contained 0.24% methyl acetate and 51.85% acetic acid. This represents 1.94 moles of acetic acid, a net production of acetic acid=1.44 moles after accounting for acetic acid in the original solution, and 0.007 mol of methyl acetate. Neither methyl iodide nor methanol was detected in the product by GC analysis.

Example 6

To a 300 mL autoclave was added 0.396 g (1.5 mmol) of $RhCl_3 \cdot 3H_2O$, 89.6 g (0.40 mol) of N,N-dimethylimidazolium iodide, 3.0 g of water, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching temperature the gas feed was switched to 100% CO and the pressure adjusted to 61.7 barg (750 psig) using 100% CO. The temperature and pressure were maintained for 5 hours using 100% CO as needed to maintain pressure. After 5 hours, the reaction was cooled, vented, and the product transferred to a sample bottle. GC analysis of the product indicated that the mixture contained 0.21 % methyl acetate, 0.76% methanol, and 57.36% acetic acid. This represents 2.26 moles of acetic acid, a net production of acetic acid=1.76 moles after accounting for acetic acid in the initial reaction zone solution, and 0.007 mol of methyl acetate along with 0.057 moles of unreacted methanol. A small amount of methyl iodide (0.38%, 0.003 mol) was detected in the product mixture by GC analysis.

Example 7

To a 300 mL autoclave was added 0.396 g (1.5 mmol) of $RhCl_3 \cdot 3H_2O$, 106.4 g (0.40 mol) of N-butyl-N'-methylimidazolium iodide, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching 190° C. the gas feed was switched to 100% CO and the pressure adjusted to 51.7 barg (750 psig) using 100% CO. The temperature and pressure were maintained for 5 hours using 100% CO as needed to maintain pressure. After 5 hours, the reaction was cooled, vented, and the product transferred to a sample bottle. GC analysis of the product indicated that the mixture contained 57.43% acetic acid. This represents 2.44 moles of acetic acid, a net production of acetic acid=1.94 moles after accounting for acetic acid in the starting reaction zone solution. No methyl iodide, methanol, or methyl acetate was detected in the product mixture by GC analysis.

Example 8

To a 300 mL autoclave was added 0.396 g (1.5 mmol) of $RhCl_3 \cdot 3H_2O$, 131.0 g (0.40 mol) of tributyl(methyl)ammonium iodide, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching 190° C. the gas feed was switched to 100% CO and the pressure adjusted to 51.7 barg (750 psig) using 100% CO. The temperature and pressure were maintained for 5 hours using 100% CO as needed to maintain pressure. After 5 hours, the reaction was cooled, vented, and the product transferred to a sample bottle. GC analysis of the product showed that the mixture contained 0.11 % methyl acetate, 0.34% methanol, and 42.69% acetic acid. This represents 1.88 moles of acetic acid, a net production of acetic acid=1.38 moles after accounting for acetic acid in the initial reaction zone solution, and 0.004 mol of methyl acetate. No methyl iodide was detected in the product mixture by GC analysis.

Example 9

To a 300 mL autoclave was added 0.396 g (1.5 mmol) of $RhCl_3 \cdot 3H_2O$, 205.4 g (0.40 mol) of trioctylmethyl phosphonium iodide, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching 190° C. the gas feed was switched to 100% CO and the pressure adjusted to 51.7 barg (750 psig) using 100% CO. The temperature and pressure were maintained for 5 hours using 100% CO as needed to maintain pressure. After 5 hours, the reaction was cooled, vented, and the product transferred to a sample bottle. GC analysis of the product showed that the mixture contained 12.15% methyl acetate, 1.81% methanol, and 11.73% acetic acid. This represents 0.60 moles of acetic acid, a net production of acetic acid=0.1 moles after accounting for acetic acid in the starting reaction zone solution, and 0.51 mol of methyl acetate. This represents a net acetyl (methyl acetate+acetic acid) production of 0.61 mol. A trace (0.19%, 0.004 mol) of methyl iodide was detected in the product mixture by GC analysis.

Example 10

To a 300 mL autoclave was added 1.39 g (1.5 mmol) of chloro tris(triphenylphosphine) rhodium, 112.0 g (0.507 mol) of N-methylpyridinium iodide, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching 190° C. the gas feed was switched to 100% CO and the pressure adjusted to 51.7 barg (750 psig) using 100% CO. The temperature and pressure were maintained for 5 hours using 100% CO as needed to maintain pressure. After 5 hours, the reaction was cooled, vented, and the product transferred to a sample bottle. GC analysis of the product showed that the mixture contained 0.63% methyl acetate and 49.64% acetic acid. No methanol was detected. This represents 2.07 moles of acetic acid, a net production of acetic acid=1.57 moles after accounting for acetic acid in the initial reaction zone solution, and 0.02 mol of methyl acetate. Only small amount of methyl iodide (0.06%, 0.001 mol) was detected in the product by GC analysis.

Example 11

To a 300 mL autoclave was added 1.39 g (1.5 mmol) of chloro tris(triphenylphosphine)rhodium, 1.18 g (4.5 mmol) of triphenylphosphine, 112.0 g (0.507 mol) of N-methylpyridinium iodide, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching 190° C. the gas feed was switched to 100% CO and the pressure adjusted to 51.7 bar (750 psi) using 100% CO. The temperature and pressure were maintained for 5 hours using 100% CO as needed to maintain pressure. After 4 hours, the reaction was cooled, vented, and the product transferred to a sample bottle. GC analysis of the product showed that the mixture contained 0.35% methyl acetate and 52.19% acetic acid. No methanol was detected. This represents 2.23 moles of acetic acid, a net production of acetic acid=1.73 moles after accounting for acetic acid in the initial reaction zone solution, and 0.02 mol of methyl acetate. Only a small amount of methyl iodide (0.05%, 0.001 mol) was detected in the product by GC analysis.

Example 12

To a 300 mL autoclave was added 0.396 g (1.5 mmol) of $RhCl_3 \cdot 3H_2O$, 117.5 g (0.50 mol) of N-ethylpyridinium iodide, 30.0 g (0.5 mol) of acetic acid, and 64.0 g (2.0 mol) of methanol. The mixture was heated to 190° C. under 17.2 barg (250 psig) of 5% hydrogen in carbon monoxide. Upon reaching 190° C. the gas feed was switched to 100% CO and the pressure adjusted to 51.7 barg (750 psig) using 100% CO. The temperature and pressure were maintained for 5 hours using 100% CO as needed to maintain pressure. After 5 hours, the reaction was cooled, vented, and the product transferred to a sample bottle. GC analysis of the product indicated that the mixture contained 0.44% methyl acetate and 51.22% acetic acid. This represents 2.14 moles of acetic acid, a net production of acetic acid=1.64 moles after accounting for acetic acid in the initial reaction zone solution, and 0.015 mol of methyl acetate. No methyl iodide or unreacted methanol was detected in the product by GC analysis.

Example 13

A 300 mL autoclave was modified to maintain a temperature control over the entire reactor, and then connected via a U tube to a high pressure condenser constructed of Hastelloy® C-276 alloy such that the vapors from the autoclave fed to the top of the chilled (20° C.) condenser. To collect the condensate, the end of the condenser was connected to a high pressure receiver constructed of Hastelloy® C-276 alloy which was equipped with a backpressure regulator at the top of the receiver to allow pressure control in the system and a valve at the bottom to allow the receiver to be drained. To the reactor/autoclave was added 2.0 g of solid $RhCl_3.3H_2O$ followed by a solution of 125 g (0.60 mol) of N,N'-dimethylimidazolium iodide in 60 g of acetic acid. The autoclave was sealed and the system was flushed first with nitrogen and then 5% hydrogen in carbon monoxide. After flushing with 5% hydrogen in carbon monoxide, the feed gas was switched to pure carbon monoxide and fed at a rate of 0.90 mol/hour with the backpressure set to maintain a pressure of 17.2 barg (250 psig) in the reactor. The reactor was heated to 190° C. and upon reaching 190° C. methanol was fed at a rate of 24 ml/hour (0.59 mol/hour, CO/MeOH mole ratio=1.5/1). The condensate was collected periodically and analyzed by GC for a period of 8 days. The daily production rate of products is summarized in Table I below wherein Temp is the temperature in ° C. of the autoclave reaction zone solution, MeI is the moles of methyl iodide detected in the product solution, MeOAc is the moles of methyl acetate present in the product solution, HOAc is the moles of acetic acid present in the product solution and Total Acetyls is the total moles of methyl acetate and acetic acid present in the product solution. The 60 grams of acetic acid added as solvent in the initial reaction zone solution was subtracted from the acetic acid present in the crude product obtained after the first day of operation. This example demonstrates the operation of the process in a continuous mode using a vapor takeoff reactor similar to that described in U.S. Pat. No. 6,916,951-B1.

TABLE I

| | | Moles of Product Produced/Day | | | |
|---|---|---|---|---|---|
| Day | Temp | MeI | MeOAc | HOAC | Total Acetyl |
| 1 | 190 | 0.0383 | 3.90 | 4.23 | 8.13 |
| 2 | 190 | 0.0053 | 1.49 | 0.57 | 2.07 |
| 3 | 190 | 0.0008 | 2.22 | 0.45 | 2.67 |
| 4 | 190 | 0.0014 | 2.56 | 0.62 | 3.18 |
| 5 | 190 | 0.0016 | 2.53 | 0.62 | 3.15 |
| 6 | 190 | 0.0046 | 2.53 | 0.80 | 3.33 |
| 7 | 205 | 0.0130 | 3.35 | 1.26 | 4.61 |
| 8 | 205 | 0.0038 | 2.27 | 0.86 | 3.13 |
| 8 Day Total | | 0.0688 | 20.86 | 9.41 | 30.02 |

Example 14

A 300 mL autoclave was modified to maintain a temperature control over the entire reactor, and then connected via a U tube to a high pressure condenser constructed of Hastelloy® C-276 alloy such that the vapors from the autoclave fed to the top of the chilled (20° C.) condenser. To collect the condensate, the end of the condenser was connected to a high pressure receiver constructed of Hastelloy® C-276 alloy which was equipped with a backpressure regulator at the top of the receiver to allow pressure control in the system and a valve at the bottom to allow the receiver to be drained. To the reactor/autoclave was added 2.0 g of solid $RhCl_3.3H_2O$ followed by a solution of 125 g (0.56 mol) of N-methylpyridinium iodide in 60 g of acetic acid. The autoclave was sealed and the system was flushed first with nitrogen and then 5% hydrogen in carbon monoxide. After flushing with 5% hydrogen in carbon monoxide, the feed gas was switched to pure carbon monoxide and fed at a rate of 0.90 mol/hour with the backpressure set to maintain a pressure of 17.2 barg (250 psig) in the reactor. The reactor was heated to 190° C. and upon reaching 190° C. methanol was fed at a rate of 24 ml/hour (0.59 mol/hour, CO/MeOH mole ratio=1.5/1). The condensate was collected periodically and analyzed by GC for a period of 8 days. The daily production rate of products is summarized in Table II below wherein Temp is the temperature in ° C. of the autoclave reaction zone solution, MeI is the moles of methyl iodide detected ion the product solution, MeOAc is the moles of methyl acetate present in the product solution, HOAc is the moles of acetic acid present in the product solution and Total Acetyls is the total moles of methyl acetate and acetic acid present in the product solution. The 60 grams of acetic acid added as solvent in the initial reaction zone solution was subtracted from the acetic acid present in the crude product obtained after the first day of operation. This example demonstrates the operation of the process in a continuous mode using a vapor takeoff reactor similar to that described in U.S. Pat. No. 6,916,951-B1.

TABLE II

| | | Moles of Product Produced/Day | | | |
|---|---|---|---|---|---|
| Day | Temp | MeI | MeOAc | HOAC | Total Acetyl |
| 1 | 190 | 0.042 | 4.37 | 4.38 | 8.76 |
| 2 | 190 | 0.011 | 4.22 | 2.31 | 6.53 |
| 3 | 190 | 0.014 | 4.32 | 2.13 | 6.45 |
| 4 | 190 | 0.022 | 4.29 | 2.91 | 7.20 |
| 5 | 205 | 0.023 | 3.90 | 4.52 | 8.42 |
| 6 | 205 | 0.026 | 4.10 | 4.45 | 8.55 |
| 6 Day Total | | 0.138 | 25.21 | 20.70 | 45.91 |

Example 15

To a 300 mL autoclave was added 0.396 g (1.5 mmol) of $RhCl_3.3H_2O$, 112.0 g (0.507 mol) of N-methylpyridinium iodide, 30.0 g (0.5 mol) of acetic acid, and 74.0 g (1.0 mol) of methyl acetate. The mixture was heated to 190° C. under 17.2 barg (250 psig) of 5% hydrogen in carbon monoxide. Upon reaching 190° C. the pressure was adjusted to 51.7 barg (750 psig) using 5% hydrogen in CO. The temperature and pressure were maintained for 5 hours using 5% hydrogen in CO as needed to maintain pressure. After 5 hours, the reaction was cooled, vented, and the product transferred to a sample bottle. GC analysis of the product showed that the mixture contained 1.31% methyl acetate, 19.55% acetic anhydride, 32.40% acetic acid, and 1.70% of ethylidene diacetate (1,1-diacetoxyethane). No methyl iodide was detected in the product by GC analysis. This example demonstrates that the process is applicable to the synthesis of acetic anhydride using methyl acetate as the carbonylation feedstock.

Example 16

To a 300 mL Hastelloy® C-276 autoclave was added 0.500 g (1.4 mmol) of Ir(CO)$_2$(acetylacetonate), 88.4 g (0.400 mol) of N-methyl pyridinium iodide, 30.0 g (0.5 mol) of acetic acid, and 64.0 g (2.0 mol) of methanol. The mixture was heated to 190° C. under 41.4 barg (600 psig) of 5% hydrogen in carbon monoxide. Upon reaching 190° C. the pressure was adjusted to 51.7 barg (750 psi) using 5% hydrogen in carbon monoxide. The temperature and pressure were maintained for 5 hours using 5% hydrogen in carbon monoxide as needed to maintain pressure. After 5 hours, the reaction was cooled, vented, and the product transferred to a sample bottle. GC analysis of the product indicated that the mixture contained 0.159 wt. % methyl acetate and 40.702 wt. % acetic acid. This represents 0.685 moles of acetic acid (Net production of acetic acid=0.185 moles after accounting for acetic acid in the original solution) and 0.002 mol of methyl acetate. Neither methyl iodide nor methanol was detected in the product by GC analysis.

The invention has been described in detail with particular reference to preferred embodiments thereof, but it will be understood that variations and modifications can be effected within the spirit and scope of the invention.

We claim:

1. Carbonylation process for the production of a carbonylation product selected from carboxylic acids, carboxylic acid esters, carboxylic acid anhydrides, and a mixture of any two or more thereof which comprises combining in a reaction zone a carbonylation feedstock compound selected from alkanols, dialkyl ethers, carboxylic acid esters, and a mixture of any two or more thereof: a Group VIII metal carbonylation catalyst comprising rhodium, iridium, or a compound thereof; an onium salt compound comprising a 1,3-dialkylimidazolium iodide or an N-alkylpyridinium iodide; and carbon monoxide under carbonylation conditions of pressure and temperature, wherein neither hydrogen iodide nor an alkyl iodide exogenous or extraneous to the carbonylation process is added or supplied to the reaction zone.

2. Carbonylation process according to claim 1 wherein the process is carried out at a total pressure of about 5 to 100 bar gauge and a temperature of about 50 to 300° C.

3. Carbonylation process according to claim 1 wherein the process is carried out at a total pressure of about 5 to 100 bar gauge and a temperature of about 150 to 250° C.; the carbonylation product is acetic acid, methyl acetate, acetic anhydride, or a mixture thereof; the carbonylation feedstock compound is methanol, dimethyl ether, methyl acetate or mixtures thereof; the Group VIII metal carbonylation catalyst is rhodium or a compound thereof; and the onium salt compound is a 1,3-dialkylimidazolium iodide.

4. Carbonylation process according to claim 1 wherein the process is carried out at a total pressure of about 5 to 100 bar gauge and a temperature of about 150 to 250° C.; the carbonylation product is acetic acid, methyl acetate, acetic anhydride or a mixture of any two or more thereof; the carbonylation feedstock compound is methanol, dimethyl ether, methyl acetate, or a mixture of any two or more thereof; the Group VIII metal carbonylation catalyst is rhodium or a compound thereof; and the onium salt compound is an N-alkylpyridinium iodide.

5. Carbonylation process for the production of a carbonylation product selected from carboxylic acids, carboxylic acid esters, carboxylic acid anhydrides, and a mixture of any two or more thereof which comprises the steps of:
   (i) feeding to a reaction zone a carbonylation feedstock compound selected from alkanols, dialkyl ethers, carboxylic acid esters, and a mixture of any two or more thereof: a Group VIII metal carbonylation catalyst comprising rhodium, iridium, or a compound thereof, dissolved in an inert solvent; an onium salt compound comprising a 1,3-dialkyl-imidazolium iodide or an N-alkylpyridinium iodide and; optionally, an inert solvent to provide a homogeneous reaction zone liquid and feeding carbon monoxide to the homogeneous reaction zone liquid under carbonylation conditions of pressure and temperature; and
   (ii) removing from the reaction zone a crude liquid product comprising carbonylation product, carbonylation feedstock compound, Group VIII metal carbonylation catalyst, onium salt compound, inert solvent and carbon monoxide;
   wherein neither hydrogen iodide nor an alkyl iodide exogenous or extraneous to the carbonylation process is added to the reaction zone.

6. Carbonylation process according to claim 5 wherein the reaction zone maintained at a temperature of about 150 to 250° C. and a total pressure of about 10 to 80 bar gauge.

7. Carbonylation process according to claim 6 wherein the carbonylation product is a carboxylic acid, carboxylic acid ester, carboxylic acid anhydride or a mixture of any two or more thereof; the carbonylation feedstock compound is an alkanol, dialkyl ether, alkyl carboxylic acid ester, or a mixture of any two or more thereof; and the homogeneous liquid reaction medium comprises about 10 to 80 weight percent carbonylation feedstock compound, about 10 to 80 weight percent carbonylation product, about 10 to 80 weight percent onium salt and about 0 to 50 weight percent inert solvent.

8. Carbonylation process according to claim 7 wherein the carbonylation product is acetic acid, methyl acetate, acetic anhydride, or mixture thereof; the carbonylation feedstock compound is methanol, dimethyl ether, methyl acetate, or mixture thereof; the Group VIII metal carbonylation catalyst is rhodium or a compound thereof; and the onium salt compound is a 1,3-dialkylimidazolium iodide.

9. Carbonylation process according to claim 7 wherein the carbonylation product is acetic acid, methyl acetate, acetic anhydride, or a mixture of any two or more thereof; the carbonylation feedstock compound is methanol, dimethyl ether, methyl acetate, or a mixture of any two or more thereof; the Group VIII metal carbonylation catalyst is rhodium or a compound thereof; and the onium salt compound is an N-methylpyridinium salt.

10. Carbonylation process according to claim 9 further comprising the steps of:
   (iii) refining the crude liquid product to recover (1) the carbonylation product, (2) a low boiling fraction comprising carbonylation feedstock compound and (3) a high boiling fraction comprising the Group VIII metal carbonylation catalyst, the onium salt compound and the optional inert solvent; and
   (iv) recycling the low boiling and high boiling fraction to the reaction zone.

11. Carbonylation process for the production of a carbonylation product selected from carboxylic acids, carboxylic acid esters, carboxylic acid anhydrides, and a mixture of any two or more thereof which comprises the steps of:
   (i) feeding a carbonylation feedstock compound selected from alkanols, dialkyl ethers, carboxylic acid esters, and a mixture of any two or more thereof and carbon monoxide to a reaction zone containing a solution comprising a Group VIII metal carbonylation catalyst comprising rhodium, iridium, or a compound thereof, and an onium salt compound comprising a 1,3-dialkylimidazolium iodide or an N-alkylpyridinium iodide to provide a homogeneous reaction zone liquid maintained under carbonylation conditions of pressure and temperature wherein the temperature of the reaction zone is maintained above the dew point of the carbonylation product; and (ii) removing from the reaction zone a crude gaseous product comprising the carbonylation product, carbonylation feedstock compound and carbon monoxide;

wherein neither hydrogen iodide nor an alkyl iodide exogenous or extraneous to the carbonylation process is added to the reaction zone.

12. Carbonylation process according to claim 11 wherein the reaction zone maintained at a temperature of about 120 to 250° C. and a total pressure of about 5 to 50 bar gauge.

13. Carbonylation process according to claim 12 wherein the carbonylation product is acetic acid, methyl acetate, acetic anhydride, or a mixture of any two or more thereof; the carbonylation feedstock compound is methanol, dimethyl ether, methyl acetate or a mixture of any two or more thereof; the Group VIII metal carbonylation catalyst is rhodium or a compound thereof; and the onium salt compound is a 1,3-dialkylimidazolium iodide.

14. Carbonylation process according to claim 12 wherein the carbonylation product is acetic acid, methyl acetate, acetic anhydride, or a mixture of any two or more thereof; the carbonylation feedstock compound is methanol, dimethyl ether, methyl acetate, or a mixture of any two or more thereof; the Group VIII metal carbonylation catalyst is rhodium or a compound thereof; and the onium salt compound is an N-methyl pyridinium salt.

15. Carbonylation process according to claim 12 further comprising the steps of:

(iii) refining the crude gaseous product to recover (1) the carbonylation product and (2) a low boiling fraction comprising the carbonylation feedstock compound; and (iv) recycling the low boiling fraction to the reaction zone.

16. Carbonylation process for the production of a carbonylation product selected from carboxylic acids, carboxylic acid esters, carboxylic acid anhydrides, and a mixture of any two or more thereof which comprises comprising the steps of:

(i) feeding gaseous carbonylation feedstock compound selected from alkanols, dialkyl ethers, carboxylic acid esters, and a mixture of any two or more thereof and carbon monoxide to a reaction zone containing a heterogeneous, solid Group VIII metal carbonylation catalyst comprising rhodium, iridium, or a compound thereof; and a heterogeneous onium salt compound comprising (1) a 1,3-dialkylimidazolium iodide or an N-alkylpyridinium iodide deposited on a catalyst support or (2) a polymeric material containing quaternary nitrogen groups wherein the reaction zone is maintained under carbonylation conditions of pressure and temperature wherein the temperature of the reaction zone is maintained above the dew point of the carbonylation product; and (ii) removing from the reaction zone a gaseous product comprising the carbonylation product, carbonylation feedstock compound and carbon monoxide, wherein neither hydrogen iodide nor an alkyl iodide exogenous or extraneous to the carbonylation process is added to the reaction zone.

17. Carbonylation process according to claim 16 wherein the reaction zone maintained at a temperature of about 150 to 250° C. and a total pressure of about 5 to 50 bar gauge.

18. Carbonylation process according to claim 17 further comprising the steps of:

(iii) refining the crude gaseous product to recover (1) the carbonylation product and (2) a low boiling fraction comprising the carbonylation feedstock compound; and (iv) recycling the low boiling fraction to the reaction zone.

* * * * *